United States Patent [19]

Jacob-LaBarre

[11] Patent Number: 5,282,851
[45] Date of Patent: Feb. 1, 1994

[54] INTRAOCULAR PROSTHESES

[76] Inventor: Jean Jacob-LaBarre, 135 Arlington Dr., Metairie, La. 70001

[21] Appl. No.: 837,483

[22] Filed: Feb. 18, 1992

Related U.S. Application Data

[63] Continuation-in-part of Ser. No. 502,458, Mar. 30, 1990, which is a continuation-in-part of Ser. No. 493,915, Mar. 14, 1990, abandoned, which is a continuation-in-part of Ser. No. 391,887, Aug. 9, 1989, Pat. No. 4,932,968, which is a continuation-in-part of Ser. No. 70,783, Jul. 7, 1987, Pat. No. 4,865,601.

[51] Int. Cl.⁵ .............................................. A61F 2/16
[52] U.S. Cl. ............................................ 623/6; 623/4
[58] Field of Search ...................................... 623/4–6, 623/66

[56] References Cited

U.S. PATENT DOCUMENTS

| | | | |
|---|---|---|---|
| 2,688,139 | 9/1954 | Jardon | 623/4 |
| 2,714,721 | 8/1955 | Stone, Jr. | 623/5 |
| 3,577,837 | 5/1971 | Bader, Jr. | 623/13 |
| 3,625,198 | 12/1971 | Sparks | 128/1 |
| 3,879,767 | 4/1975 | Stubstad | 623/21 |
| 3,988,782 | 11/1976 | Darkik et al. | 3/1 |
| 3,992,563 | 11/1976 | Tanaka | 526/219 |
| 4,285,073 | 8/1981 | Szycher | 623/6 |
| 4,355,426 | 10/1982 | MacGregor | 623/66 |
| 4,400,833 | 8/1983 | Kurland | 623/11 |
| 4,409,691 | 10/1983 | Levy | 3/13 |
| 4,452,776 | 6/1984 | Refojo | 623/4 X |
| 4,536,179 | 8/1985 | Anderson et al. | 604/266 |
| 4,549,529 | 10/1985 | White | 128/1 |
| 4,612,012 | 9/1986 | White | 623/5 |
| 4,647,282 | 3/1987 | Fedorov et al. | 623/4 |
| 4,715,858 | 12/1987 | Lindstrom | 623/5 |
| 4,806,382 | 2/1989 | Goldberg et al. | 623/4 |
| 4,865,601 | 9/1989 | Caldwell et al. | 623/5 |
| 4,932,968 | 6/1990 | Caldwell et al. | 623/6 |

FOREIGN PATENT DOCUMENTS

| | | |
|---|---|---|
| 0136807 | 4/1985 | European Pat. Off. |
| 0224460 | 6/1987 | European Pat. Off. |
| 2705234 | 8/1978 | Fed. Rep. of Germany ......... 623/5 |
| 3609910 | 10/1987 | Fed. Rep. of Germany ........ 623/11 |
| 2601872 | 1/1988 | France. |
| WO90/00887 | 2/1988 | PCT Int'l Appl. ............... 623/11 |
| WO88/02622 | 4/1988 | PCT Int'l Appl. |
| 2124500 | 2/1984 | United Kingdom. |

OTHER PUBLICATIONS

Choyce, D. P.: "Orbital Implants". *Brit. Ophthal.* (1952) 36, 123–130.

Przybyla, Jr., Vincent A. et al.: "Complications Associated with Use of Tantalum-Mesh-Covered Implants". Ophthalmology 89: 121–123 (Feb. 1982).

Smolin, Gilbert and Richard A. Thoft, Eds. *The Cornea.* Boston: Little, Brown & Co. (1983) pp. 429–430, 450–453.

Karesh, James W.: "Polytetrafluoroethylene as a Graft Material in Ophthalmic Plastic and Reconstructive Surgery". Ophthalmic Plastic and Reconstructive Surgery 3 (3): 179–185, 1987.

*Primary Examiner*—Randy C. Shay
*Attorney, Agent, or Firm*—Pravel, Hewitt, Kimball & Krieger

[57] ABSTRACT

An intraocular prosthesis (56) for implanting in an annular void extending radially into the tissues of the eye. The prosthesis is a circular, transparent, elastomeric optical element (57) having a peripheral edge and a non-rigid or flexible porous skirt (68) which extends radially from the periphery of the element. The skirt encircles the element and is positioned to extend radially into the void. An annular, flexible porous portion (68) having a pore size in the range of about 15–90 microns, and preferably about 60 microns, is included with the skirt. The porous portion surrounds the element and is disposed in contact with the tissues of the eye surrounding the void to allow fibrous growth into the pores of the porous portion. A plurality, preferably, six, spoke-like, porous extension (54) may be included.

9 Claims, 5 Drawing Sheets

INTRAOCULAR PROSTHESES

CROSS REFERENCE TO RELATED APPLICATIONS

This is a continuation-in-part of copending U.S. patent application Ser. No. 07/502,458, filed Mar. 30, 1990. This is also a continuation-in-part of copending U.S. patent application Ser. No. 07/493,915, filed Mar. 14, 1990, now abandoned, which is a continuation-in-part of U.S. patent application Ser. No. 07/391,887, filed Aug. 9, 1989, now U.S. Pat. No. 4,932,968, which is a continuation-in-part of U.S. patent application Ser. No. 07/070,783, filed Jul. 7, 1987, now U.S. Pat. No. 4,865,601. All of these applications are hereby incorporated by reference.

BACKGROUND OF THE INVENTION

1. Field of Invention

This invention relates to intraocular optical lenses. More particular this invention relates to a prosthesis for replacing a part of the cornea of the eye, which has suffered for example several corneal damage, and relates to a prosthesis for replacing the posterior lens of the eye which has variable power.

2. Prior Art and General Background

There are many cases of corneal blindness, caused by severe alkali burns, immunological disorders (e.g. Stevens-Johnson syndrome) cicatrical mucous membrane pemphigoid, or severe dry eyes where regular keratoplasty is not practical or has repeatedly failed. These corneas are often grossly opaque and densely vascularized with uneven thicknesses, associated with dense anterior and posterior synechiae, shallow or flat anterior chambers and cataracts or aphakia. In these situations only replacement of the cornea by a penetrating static keratoprosthesis effectively helps the patient. Current prosthetic designs require living tissue to bind to, through and around a hard polymethylmethacrylate (PMMA) prosthesis.

Keratoconus is a progressive disease of the cornea, which often results in an outward protrusion of the central area of the cornea, causing a thinning and disfigurement of the central cornea tissue. Since the cornea is basically a refracting surface for light rays received from the atmosphere, if the cornea is diseased with keratoconus, the resulting protrusion or cone distorts the normal refracting of the light rays, causing poor visual acuity and distortion. In addition, keratoconus is often very painful and irritable for the patient.

There are two known basic techniques which may be used to control or correct keratoconus. A first, more conventional technique, such as described in Siviglia, U.S. Pat. No. 4,601,556 issued on Jul. 22, 1986, is to fit the patient with a special contact lens having a back or posterior surface, which is specifically designed to permit the diseased portion of the cornea to conform itself to the lens surface, resulting in both control of the keratoconus disease and improved visual acuity. Obviously, if the disease can be successfully controlled or corrected using such a special contact lens, a surgical corneal transplant can be avoided. However, for those cases in which the disease cannot be successfully controlled or corrected using a special contact lens, a surgical corneal transplant will be necessary.

Keratoplasty or corneal transplantation is a replacement of a partial (lamellar) or full (penetrating) thickness of diseased host cornea with donor tissue. Penetrating or lamellar keratoplasty may remove either a segment of, partial keratoplasty, or the entire, total keratoplasty, cornea. Improved techniques in cornea preservation, micro surgery and postoperative management have greatly increased the prognosis for penetrating keratoplasty during the past ten years. Previously "forbidden" corneal disorders are now being grafted successfully.

Although penetrating keratoplasty is quite successful, several factors can compromise the success of any graft. These include lid abnormalities, tear dysfunction states, recurrent forms of conjunctival inflammation, trigeminal dysfunction and neurotrophic keratitis, stromal vascularization, irregularities or extreme thinning of the stroma at the proposed graft-host junction, severe structural alteration to the anterior segment, active microbial or inflammatory keratitis, uncontrolled glaucoma and infancy.

When repeated grafts have failed, it is possible in an otherwise hopeless case to restore some vision by inserting a keratoprosthesis.

Initially the keratoprosthesis included a rigid, fenestrated, supporting plate with a removable threaded hard optical cylinder. The fenestrations or openings were to permit ingrowth of connective tissue and improve nutrition of the anterior corneal layers. Advances in this particular art led to a mushroom shaped transcorneal keratoprosthesis, such as that described in U.S. Pat. No. 4,470,159 to Peyman issued on Sep. 11, 1984. However, posterior fibrous coverings tend to extend over the optical portion, thus clouding of vision or even blindness may result, and inadequate anterior anchoring and ingrowth persists, and, although some prosthesis have remained successfully in place for years, others have been extruded in only weeks or months.

At the present time, the most commonly used prosthesis is an implant of a hard solid cylindrical polymethylmethacrylate lens in a flanged tubular element that protrudes posteriorly deep into the anterior chamber of the eye and which has biconvex anterior and posterior surfaces, forming a lens of appropriate power. The major complication with implants of this methylmethacrylate lens or "button" variety is that a firm bond between the cornea and the implant does not develop, and thus no barrier to infection from pathogens, which seems to occur subsequent to aqueous humor leakage from the anterior chamber around the optical center, is established, leading to extrusion with resulting endophthalmitis and blindness. Secondary glaucoma may also be severe complication with this type of prosthesis, because of the destruction of the outflow tracks. Thus the inability of corneal tissue to adequately infiltrate the edges of the implant to effect stabilization of the prosthesis and prevent aqueous humor leakage is a cause of many failures of these prostheses.

Attempts have been made to provide a keratoprosthesis having a softer, more porous substrate surrounding the periphery of the cylindrical lens in the remaining lamellar cornea tissues. For the substrate, the patient's own tooth material, osterodentoceratoprostease, was used to provide the supporting structure.

Attempts have also been made to use a dacron peripheral skirt and supportive ungainal material, which have met with some postoperative success. Attempts have also been made to use a dacron velour skirted implant, but implants of this type have generally yielded unsatisfactory results. Perforations have also been replaced with radial slits, with gave for some of these embodiments better ingrowth results. However, good long term results were only obtained when implantation was accomplished by a slow surgical procedure requiring three operations, six to eight weeks apart. Although, these offered a slightly better visual field range, the prosthesis basically has a limited field of vision of less than fifty percent.

Attempts have also been made to employ a vitreous carbon alloplast, which is an inert carbon and "Teflon" mixture, as the material for anchoring corneal implants. The results, however, have been found less significant.

Cardona has also provided an implant having a flexible supporting plate, which improved the prosthesis ability to conform to corneal contours. The optical cylinder of the Cardona implant is threaded with an interpigmented cord to reduce glare. Extrusion of this type of prosthesis has been reduced in patients with thin corneas and pore conjunctiva, by having the central optical portion pass through the upper eyelid as well. The central optical element of this type of implant has been softened using a hydrogel disc in the cylindrical optic but with a rigid skirt, an example of this being the "hydrogel keratoprosthesis" of Binder (U.S. Pat. No. 4,586,929 issued on May 6, 1986), having the same anchoring problem previously discussed.

It is also known that polyglycerl methacrylate, a much softer and more hydrophilic polymer than polymethylmethacrylate, produced little or no implanatory changes in the cornea or interior chambers. However problems regarding suitable anchorings still persist.

Non-toxic silicone-rubber implants have also been encapsulated, and a ceramic keratoprosthesis having a ceramic form of alumina oxide with traces of magnesium oxide ($Al_2O_3$ 99.7% $MgO$ 0.3%), which has a high refractive index and high wetability, has been relatively successful. However, anchoring the implant poses some difficult problems. Even with the use of sutures and cyanoacrylate glue, intermittent leakage of fluid around the cylinder has led to infection and extrusion.

Presently keratoprostheses are supported initially by sutures which are augmented by periosteum, fascia lata, Tenon's capsule and/or conjunctival flaps. Further, a significant amount of all keratoprosthetic operations requires some type of sutury operation, since complications due to uncontrollable glaucoma, optical overgrowth, conjunctival retraction, uveitis, retroprosthetic membranes and endophthalmitis are still prevalent, and the long-term visual acuity drops to little or no light perception in great than 50% of all the cases. Therefore, while the extrusion rates of keratoprosthetic devices have dramatically decreased, a successful implant material has not been found, which can mimic corneal properties enough to allow easy anchoring and adequate ingrowth in the eye. Without this, the prosthesis will ultimately fail.

For a corneal implant which is entirely embedded in the cornea and which is not exposed to the atmosphere nor to the aqueous humus, see U.S. Pat. No. 4,607,617 to Choyce issued on Aug. 26, 1986. The corneal implant allows correction for defects in eyesight normally corrected by spectacles and contact lens and provides a surgical alternative to mitigate the defective eyesight Another type of disease, which may affect an intraocular element of the eye, is cataracts. A cataract is a progressive disease of the posterior lens behind the iris of the eye, causing clouding of the lens or of its surrounding transparent membrane that obstructs the passage of light. Since the posterior lens is basically an element for generating an image by focussing rays of light through the vitreous chamber and onto the retina in the back of the eye, which is varied by muscles within the eye, to focus on objects that are close or far away, the resulting clouding of the element causes eventual blindness.

It has been found possible to alleviate this condition by providing a static clear, hard disc having convex anterior and posterior surfaces, which is inserted into the eye and located in the capsular bag between the iris and the vitreous body, along with removal of the posterior lens (lensectomy) of the eye. As described in U.S. Pat. No. 4,615,701, these may be provided with haptics or flexible strands, which curve outward from the periphery of the lens that may be positioned close to the lens optic for ease of implantation and which are then released to move to the peripheral limits of the lens capsule, for centration and fixation of the intraocular lens for attaching the lens to the ciliary body which encircles the lens.

In some cases the disc is somewhat flexible and the ciliary body may provide some focussing control over the lens by means of the haptics. However, any control over this type of artificial lens is generally limited and may not provide adequate focussing of the lens to restore optimal vision to the patient. Further, with an artificial lens which is hard, additional refractive lens are necessary for good vision, as the hard disc is structurally adequate for optimum vision only at a single, set focal point.

Some attempts have been made to provide an intraocular prosthesis that provides accommodation in response to contraction and relaxation of the ciliary body. Accommodation is achieved by the motion of a lens or an element of a lens system, which have been implanted in a capsule, alternately toward and away from the fovea. Radially extending struts are provided which are biased radially inward, as the ciliary body contracts, forcing the lens toward the fovea, so that when the ciliary body is fully relaxed the lens is at its closest position to the fovea, and, as the ciliary body contracts, it counters the bias and causes the lens to move away from the fovea and toward the cornea.

For an example of a posterior lens of this type having a lens system implanted in a capsule, see U.S. Pat. No. 4,409,691 to C. F. Levy issued on Oct. 18, 1983. For another example of an intraocular lens that provides accommodation and response to contraction and relaxation of the ciliary body, see for example U.S. Pat. No. 4,373,218 to R. A. Schachar issued on Feb. 15, 1983.

In the Schachar patent is described an intraocular lens having a fluid-expandable sack for containing a fluid. The fluid-expandable sack includes a lens portion and a valve portion which extends through the sclera of the eye. The fluid-expandable sack contains a fluid therein for providing the desired index of refraction, which may be either a gas or a liquid, and the index of refraction of the posterior chamber intraocular lens may be changed by adding or withdrawing fluid from the lens. However, no means is provided for attaching the lens element to the ciliary body and complications such as extrusion, retinal detachment and cystoid macula edema may still occur.

For additional patents relating to intraocular lens, see U.S. Pat. Nos. 4,615,701 to Woods issued on Oct. 7, 1986, 4,615,702 to Koziol et al. also issued Oct. 7, 1986, and 4,616,700 to Fedorov et al. likewise issued Oct. 7, 1986.

Accordingly, it is an object of the method and apparatus of the present invention to provide an improved keratoprosthesis for the replacement of the diseased or injured cornea, which method and apparatus differs from prostheses in current use, in that it does not protrude into the inner eye, but rather lies deep in an intralamellar stromal pocket and which is anchored in placed by a fibrous ingrowth of tissue into an annular porous portion forming the periphery of the prosthesis. In accordance with this object, the method and apparatus of the present invention provides a lens or prosthesis having a convex anterior surface and a concave posterior surface, which has an annular porous ingrowth skirt extending radially from the periphery of the optic which, when optic positioned in an annular corneal incision extending annularly into the stroma of the cornea, allows fibrous ingrowth of the tissue into the skirt, thus anchoring the prosthesis in the sclera.

Further, the method and apparatus may provide spoke-like porous extensions, which are spaced around the periphery of the skirt and which extends radially therefrom and which are positioned in tunnels in the stroma of the cornea, which extend through the limbus into the sclera for allowing the forward progression of fluid from the anterior chamber to allow adequate nutrition and to avoid degeneration of the corneal connective tissue and corneal stroma of any remaining corneal tissue.

A further object of the keratoprosthesis is to provide a firm bond between the cornea and the prosthesis, so that no aqueous fluid can leak past the implant and therefore there is no direct entrance for pathogens into the eye. A further object of the keratoprosthesis is to provide a prosthesis having a similar disposition as the cornea of the eye, so that the patient may have a greater visual field and physicians may have a larger window for inspection on the inner eye. It is still a further object of the keratoprosthesis that no epithelial cells grow over its optic center and that the prosthesis-corneal shearing force has been eliminated, therefore eliminating extrusion. Another object of the keratoprosthesis is that the patient has a better cosmetic appearance.

A further object of the method and apparatus is to provide a prosthesis lens which may be inserted into the eye and located in the capsular bag between the iris and the vitreous body for replacement of the posterior lens of the eye. Further, it is an object of the invention to provide a prosthesis for replacement of the posterior lens of the eye which is flexible and can be placed in the lens capsule, which surrounds the posterior lens of the eye, so that the lens element will change shape in response to ciliary body contraction in a similar manner as the normal posterior lens of the eye would.

3. General, Summary Discussion of the Invention

In accordance with these objects, the prostheses of the present invention provide an elastomeric optical element having an annular skirt which surrounds the periphery of the element. Included with the skirt is an annular porous portion. The optical element is attached to the skirt by interpenetration of the periphery of the optical element into the pores of the porous portion.

The optical element may include convex anterior and posterior surfaces for replacement of the diseased or injured corneal button of the eye. An annular porous portion extending radially outwardly to periphery of the skirt is disposed in a lamellar incision which extends annularly into the stroma of the cornea surrounding the corneal button which is to be replaced.

A plurality of porous extensions, which may be six, extend radially outward from the periphery of the skirt and are located in tunnels extending radially through the limbus into the sclera. The extensions are entirely embedded and are not exposed to the atmosphere and allow forward progression of fluid by means of their pores from the anterior chamber of the eye to the sclera, thus allowing adequate nutrition of the sclera while avoiding degeneration of any remaining corneal stroma.

Tissue ingrowth into the pores of the porous portion connects and surrounds the prosthesis to the remaining corneal tissues, thus preventing aqueous fluid from leaking past the implant while allowing no direct path for pathogens into the eye.

The optical element may include biconvex anterior and posterior surfaces for replacement of the posterior lens of the eye between the iris and the vitreous body. Firstly, a small incision is made. Secondly, the natural lens of the eye can then be removed by any method such as lensectomy or cryoextraction. Thirdly, the prosthesis is inserted through the incision and the opening in the iris and manipulated into the capsular bag.

The removal of the natural lens forms a void in the eye which is surrounded by the lens capsule, in which the prosthesis may be located, with its annular skirt in contact with the internal surface of the lens capsule (or capsular bag). Once the prosthesis has been manipulated into position, the incision may be sutured closed, allowing the prosthesis to stabilize in the lens capsule, and to connect to the lens capsule through fibrous ingrowth into the pores of the porous portion of the skirt.

An ocular prosthesis can be made for use as an implant within the eye or on the outer surface, at least in part of a non-resorbable non-dissolving porous polymer material for forming a tissue attachment and/or ingrowth within the eye. The prosthesis body can have tissue ingrowth and/or tissue adhesion means for forming a bond between the eye tissue and the prosthesis wherein the body and ingrowth means comprise a portion formed of a porous polymer material.

A total ocular prosthesis comprises a prosthesis body that includes in part a coating or layer of a porous polymer for forming a tissue ingrowth and/or adhesion attachment with ocular muscles. The polymer is preferably of a polymer material that will not unravel when cut.

Each prosthesis is adapted to form attachment to eye muscle tissue. One prosthesis can be an ocular replacement with muscle attachment sites thereon.

The prosthesis can include means thereon for scleral reinforcement. The prosthesis can be in the form of a scleral buckle. The prosthesis can be in the form of a glaucoma drain. The prosthesis can be in the form of an epikeratophakia lenticle. The prosthesis can be in the form of a lacrimal duct drain.

In one embodiment, the polymer forms a porous layer and there is an adjacent non-porous layer so that a barrier is defined against bacterial penetration or fluid leakage. The both sides thereof. The non-porous layer is preferably of a polymer material. The non-porous layer is preferably a non-porous polyurethane.

BRIEF DESCRIPTION OF THE DRAWINGS

For a further understanding of the nature and objects of the present invention, reference should be made to the following detailed description, taken in conjunction with the accompanying drawings, in which like parts are given like reference numerals, and wherein:

FIG. 1 is a side, cutaway view of the eye; while

FIG. 5 is a side, cutaway view of the eye with the first embodiment (FIGS. 3 and 3A) implanted; while

DETAILED DESCRIPTION OF THE PREFERRED EXEMPLARY EMBODIMENTS

GENERAL, OCULAR BACKGROUND

Figure 1:
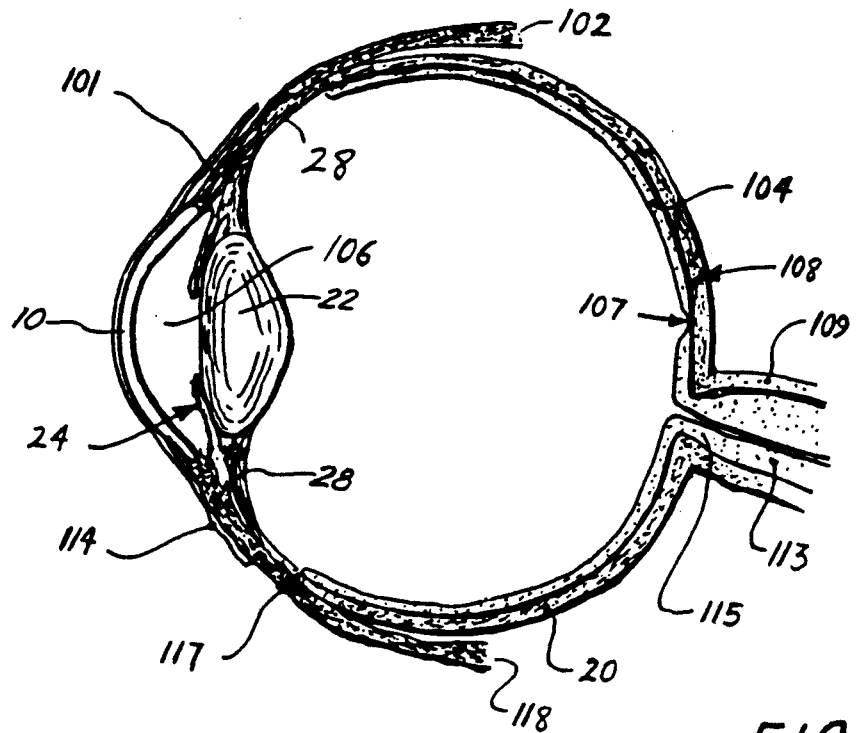
Figure 2:
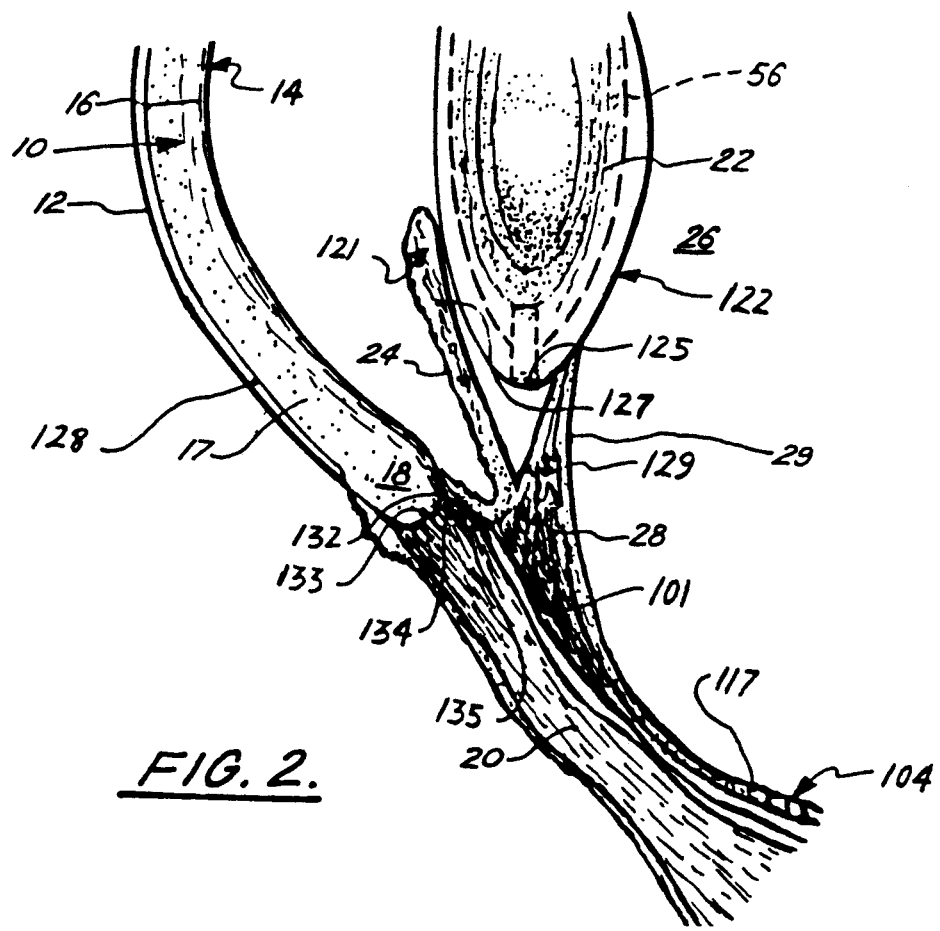
FIG. 2 is a side, cutaway detail of the eye.

Referring to FIGS. 1 and 2, a cross-sectional view of the human eye is shown, so that the location and arrangement of the interior ocular element of the eye may be referred to.

As general background, the eye has a hemispherical shaped cornea 10, which extends laterally from the corneal epithelium 12 to the corneal endothelium 14. Extending laterally over the anterior surface of the corneal endothelium 14 is a hemispherical shaped membrane, known as Descement's membrane 16, which separates the body or stroma 17 of the cornea 10 from the corneal endothelium 14.

Surrounding the periphery of the cornea 10 is an annular portion called the limbus 18. The cornea 10 along with the limbus 18, are positioned in an opening in the sclera 20, with the tissues of the sclera 20 interconnecting with the limbus 18.

Behind the posterior surface of the cornea is the posterior lens 22. The lens 22 is positioned in a pocket 23 between the iris 24 and the vitreous body 26 of the eye. Between the iris 24 and the vitreous body 26 an annularly shaped portion known as the ciliary body 28 is found. The ciliary body 28 includes the ciliary muscle 101, ciliary prosthesis and zonular fibers 29 which interconnect with the circularly periphery of the lens capsule 122 so that the lens may change shape in response to ciliary body 28 contraction.

Also shown in FIGS. 1 and 2 are lateral rectus 102, retina 104, anterior chamber 106, fovea 107, choroid 108, dural sheath 109, optic nerve 113, bulbar conjunctiva 114, lamina cribrosa 115, ora serrata 117, medial rectus 118, Sphincter pupillae 121, lens capsule (or capsular bag) 122, lens epithelium 125, pigment layer 127, Bowman's membrane 128, ciliary processes 129, corneoscleral trabeculum 133, canal of Schlemm 134, and scleral spur 135.

The function and interrelationship of these components of the eye are well known and for that reason a detailed explanation of each component, other than that provided, will not be provided herein. Hence, with a general understanding of the intraocular construction of the eye, the detailed description of the preferred exemplary methods and prosthesis of the present invention may be set forth.

In general, the prosthesis may be implanted in an annular void, which extends radially into the tissues of the eye generally between the anterior surface of the cornea 10 of the eye and the posterior surface of the lens capsule 122 of the eye. The prosthesis allows for the replacement of for example a diseased intraocular portion of the eye which is removed therefrom as discussed in the following.

The prosthesis includes a circular transparent ocular element which is elastomeric and preferably clear. The element may be made from any suitable material such as for example a polymer, with suitable types of polymer being a hydrophilic urethane, a strong hydrogel/hydrophilic urethane copolymer or interpenetrating network polymer, a strong hydrogel or a hydrophilic silicone, a fluoropolymer, cellulose acetate butyrate or other like material that can be cast or formed.

Figure 7:
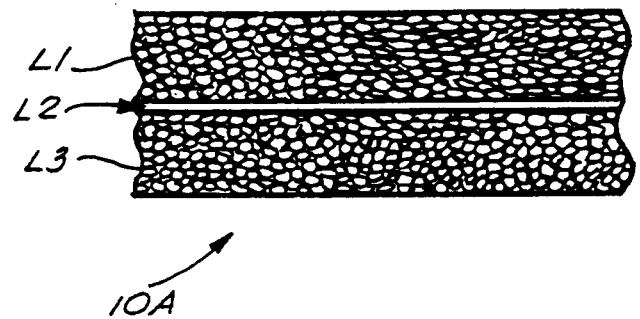
FIGS. 7-9 are schematic diagrams illustrating the layering of porous and non-porous layers of material used with the prostheses of the present invention.
Figure 8:
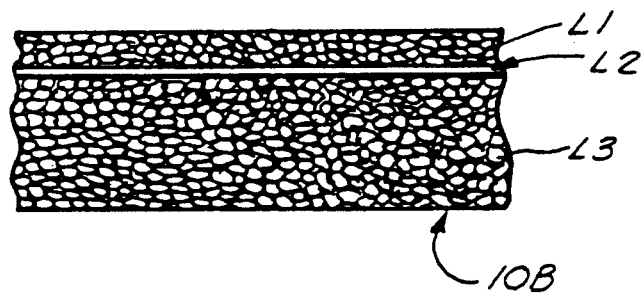
Figure 9:
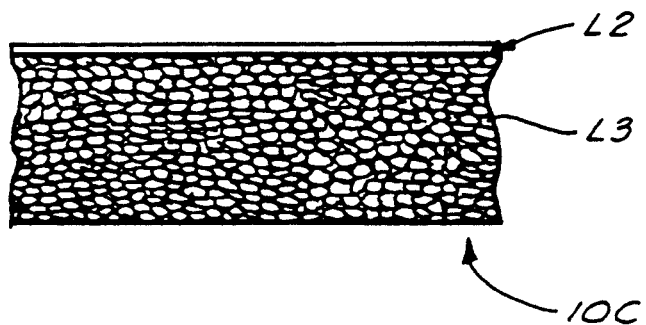

FIGS. 7, 8, and 9 illustrate schematically examples of layering of the porous and non-porous layers. A prosthesis, designated respectively as 10A in FIG. 7 and 10B in FIG. 8, includes a non-porous layer L2 forms an internal layer with porous polymer layers L1 and L3 positioned on both sides of the layer L2. In FIG. 9, a prosthesis 10c having a porous polymer layer L3 abuts on one side a non-porous polymer layer L2.

Many prosthetic devices of the eye need to be anchored into the adjacent tissue to secure the prosthesis in place over time and prevent extrusion. Anchoring can be difficult since for best results the compliance of the anchoring portion of the device must be near that of the tissue. The compliance of metal is very different from tissue, so tissue tears away from metal under stress. The ocular prostheses of the present invention have porous polymer portions for ingrowth and attachment of the surrounding tissue to the prosthesis. Since compliance of the polymer material is similar to tissue, it does not easily tear away from the ingrown and attached tissue. The average size of the pores in the polymer material can range from 20 to 90 microns. The configuration of the pores in the polymer material may be different for different prosthetic applications. The configuration can be manipulated by the manufacturing techniques. The porous polymer material can be attached to the rest of the prosthesis or can comprise the entire prosthesis.

One configuration, similar to the one shown in FIG. 9, but without layer L2, is that of a completely porous polymer material. This allows cellular ingrowth and attachment to concur completely throughout the porous polymer layer L3. Cell introduction can occur through all sides of the polymer material in layer L3 except where it is attached to the rest of the prosthesis. This material is useful for internal ocular prostheses where tissue anchoring is desired.

A second configuration, shown in FIGS. 7 and 8, is that of a porous polymer material (in layers L1 and L3) that has an internal non-porous layer L2 so that while ingrowth can occur from the anterior and posterior sides of the polymer there is no direct porous communication between the anterior and posterior sides. The non-porous layer L2 acts as a barrier against bacterial penetration or fluid leakage while the tissue is ingrowing and throughout the life of the prosthesis. This configuration is useful in scleral augmentation, conjunctival and corneal applications where complete security from an open globe situation is desired.

A third configuration, shown in FIG. 9, is that of a porous polymer material (in layer L3) with a non-porous side (layer L2). The pores may be of an average size or get progressively smaller as they approach the non-porous side L2. The non-porous side L2 may be surface grafted to change its hydrophilicity or be comprised of a more hydrophilic polymer than the porous portion L3 of the material. The material may be produced in a sheet or as a small diameter tube. In the tubular form it is a one-piece, ingrowth anchorable, tube with a non-porous inner surface and a porous outer surface, which can be used for fluid drainage applications such as glaucoma drains or lacrimal ducts.

The major manufacturing techniques used to make the porous polymer material are in the public domain such as electrostatic spinning and the Wong-Lightner technique. The polymer used to produce the porous material can be a polyurethane, polypropylene-polybutylene copolymer, polytetrafluoroethylene, or an acrylate or silicone based polymer. The porous material may be grafted or coated to protect the polymer from oxidation or with peptides or proteins such as fibronectin, collagen or composites to promote and enhance cellular infiltration and attachment.

Figure 3:
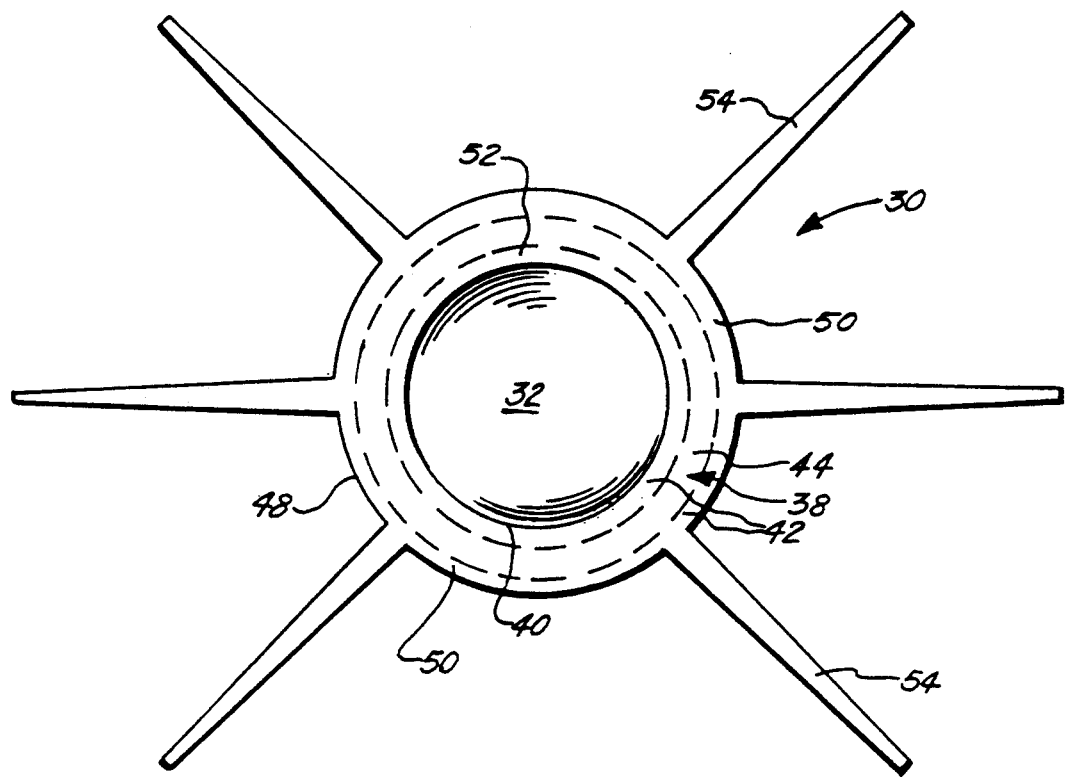
FIG. 3 and 3A are front and side, cross-sectional views, respectively, of a first, preferred, exemplary embodiment of the prostheses of the present invention.
Figure 4:
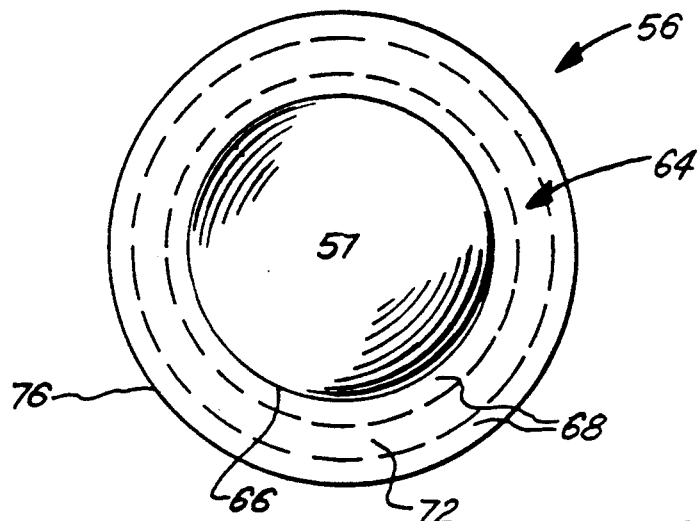
FIGS. 4 and 4A are front and side, cross-section views, respectively, of a second, preferred, exemplary embodiment of the prostheses of the present invention.

The material described above and shown in FIGS. 7, 8, and 9 (and including the material similar to that shown in FIG. 9, but without layer L2), can be used as the flexible attachment means for the prostheses shown in FIGS. 3 and 4.

FIRST KERATOPROSTHESIS EMBODIMENT

FIGS. 3, 3A & 5

Figure 3A:
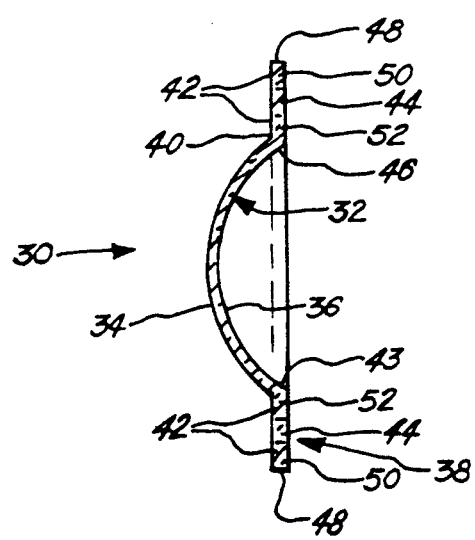

Referring to FIGS. 3 and 3A, an embodiment of the prosthesis 30 suitable as a keratoprosthesis is shown. The prosthesis 30 includes an elastomeric element, which is generally hemispherically shaped, having a diameter generally eight millimeters.

The hemispherically shaped element 32 includes a convex anterior surface 34 having a radius of curvature generally for example 7.9 millimeters to insure good tear flow and lid closure and a concave posterior surface 36. The radius of curvature for the concave posterior surface 36 controls how the power of the optic is determined and is dependent upon each patient's eye. Preoperatively the radius of curvature for the posterior surface may be determined for example, by performing an ultrasound scan and/or evaluating the patient's refraction and then making a clinical estimate of the proper power of the optic in order to determine proper refraction of the eye.

The elastomeric optical element 32 is preferably made from a hydrophilic, optical polyurethane having a high elastic modulus and tensile strength. A suitable, exemplary polyurethane is BPS-300 as supplied by Mercor, Inc., 2448 6th St., Berkley, Calif. 94710.

The polyurethane is preferably tested by two exemplary analytical methods. A sample of it may be shot through for example a GPC column at 60 degrees centigrade using dimethylacetamide with 0.5 percent lithiumbromide. The sample preferably gives acceptable peak results, and an infrared spectrum is then taken on another sample to insure a polyurethane linkage fingerprint.

An annular skirt 38 extends radially from the peripheral edge 40 of the ocular element 32 and encircles the element 32. The annular skirt 38, may be made of for example fluorocarbon having a low coefficient of friction such as polytetrafluoroethylene. A suitable, thin, porous, polytetrafluoroethylene sheet with an average pore size of 60 microns is "Goretex" obtained from W. L. Gore's & Associates, Inc., of Flagstaff, Ariz. The skirt 38 preferably has a diameter of for example 18 millimeters and a thickness of 0.5 millimeters. The material is examined microscopically for clean, inclusion-free pores, and the matrix tensile strength is measured for minimum strength.

An annular porous portion 42 is included with the skirt 38 and surrounds element 32. As may be appreciated, the polytetrafluoroethylene provides the porous portion and in general has for example a pore size of 20-90 microns, which have been found suitable for purposes which are discussed below. The skirt 38 is circular and has a central opening 43, in which the optical element 32 is disposed.

The optical element 32 is permanently mated to the skirt 38 during the formation of the intraocular element 30. In general, this is accomplished by centering the annular skirt 38 between a pair of opposed hemispherical molds, having facing convex and concave surfaces, and clamping the molds together with the annular skirt 38 sandwiched between the molds. A polymerization mixture is then introduced into the space between the molds, which overlap radially into the porous material for forming the lens. The overlapping polymerization mixture, which extends annularly around the inner portion of the skirt 38, is allowed to interpenetrate into the porous material for bonding the optical element 32 to its skirt 38.

A preferred embodiment for the skirt 38 has an annular portion 44, which is compressed by any suitable means and extends around the skirt 38. The annular portion 44 is located radially outward from the inner periphery 46 of the skirt 38 and radially inward from the outer periphery 48 of the skirt 38.

By compressing a portion of the skirt 38, a closed pore barrier 44 having a radial thickness of one millimeter may be formed which extends around the skirt 38 between its inner and outer peripheries 46, 48. Hence, suitable exemplary dimensions for the skirt 38 after compression would be for example a two millimeter radial thickness of annular open pore ingrowth space 50, which extends radially inward from the outer periphery 46 of the skirt 38; a one millimeter radial thickness annular closed pore barrier 44; and a one millimeter radial thickness open pore annular bonding portion 52, which extends radially outward from the inner periphery 46 of the skirt 38 and which surrounds opening 43 for interpenetration and bonding of the lens element to the skirt 38.

Accordingly, the closed pore barrier 44 will prevent fluid communication between the ingrowth space 50 and the open pore annular bonding portion 52. For exemplary purposes and as may be appreciated, the central opening 43 may be formed in the exemplary thirteen millimeter diameter skirt 38 by any suitable means, such as for example an eight millimeter trephine, and the pores at a one millimeter radius from the trephined opening 43 in a one millimeter wide ring outward may be compressed closed to form the closed pore barrier 44 by using for example a warm press.

A plurality of equidistantly spaced, spoke-like extensions or haptics 54 may extend radially outward from the periphery 48 of the skirt 38. The extensions 54 are likewise porous as the ingrowth space 50 and have a similar pore size of for example twenty-five to sixty microns. Preferably, there are six, spoke-like extensions 54, which are spaced equidistant and radiate outward from the skirt 38.

Each haptic 54 may be formed by making suitable radial and arcual shaped cuts in the skirt 38 conjunctively, thus integrally forming both the skirt 38 and the extensions 54. Exemplary, each extension 54 may be approximately ten millimeters long, for purposes which will be mentioned later, and have a transverse width of for example two millimeters.

The keratoprosthesis is preferably formed under suitable conditions which may include chemical and clean air hoods, in which the prosthesis is made. The optical element 32 is preferably cast in for example Aldrich "Gold Label" dimethyl acetamide on a radially curved mold in the present of the skirt 38 at generally ninety degrees centigrade in a convention oven, which has been placed in forced air hood. For obtaining the extra power necessary for an individual patient, the prosthesis optic is then thermoset between two molds of the desired radial curvature, which are of for example precision cut brass and which are for example nickel chrome plated.

Using for example Gullstrand's miotic eye and the optical equation for the first forder refraction as a spherical interface, the parameters may be calculated. Hence, with allowance for the index of refraction of the intraocular element, which may differ from the index of refraction of the cornea, the physical properties or measurements of the intraocular element 30 may be calculated. In calculating these measurements, ultrasound of the patient's eye gives the internal distances for use in the calculation. These values may then be calculated by hand or by using any suitable means such as a computer which runs a series of iterations on the optic equation for the first order of refraction at a spherical interface, until it generates an inner corneal radius of curvature that gives the best diopters result.

The prosthesis 30 may then be fully equilibrated in saline and sterilized in hydrogen peroxide before implantation.

For implanting, the patient is anesthetized, a seven millimeter corneal trephine is centered over the cornea of the diseased eye, and a circular corneal incision is made using the trephine. The corneal incision may extend as deep as Descemet's membrane.

Using a knife such as a Gills knife, a lamellar incision may be made which extends radially into the stroma of the cornea and annularly around the walls of the corneal incision. As may be appreciated, the lamellar incision may extend as deep as the limbus. The corneal tissue surrounding the lamellar incision may then be separated to form an annular void.

Again using a knife such as a Gills knife, a plurality of tunnel incisions equaling the number of extensions 54 are cut, which extend radially into the stroma through the limbus and into the sclera for a distance of approximately one millimeter. Radial scleral incisions are then made over the tunnels, and the extensions 54 of the prosthesis 30 are thus placed into the tunnels except for two extensions 54.

Hence a suitable space between the prosthesis 30 and the cornea remains, allowing the anterior chamber to be then entered for removing the corneal button between the walls of the circular incision. After removal of the corneal button, the two remaining extensions 54 are then carefully placed in the tunnels, and the anterior chamber is reformed with healon.

The extensions 54 are then sutured in the limbus region with a suitable filament such as for example 10-0 nylon.

Figure 5:
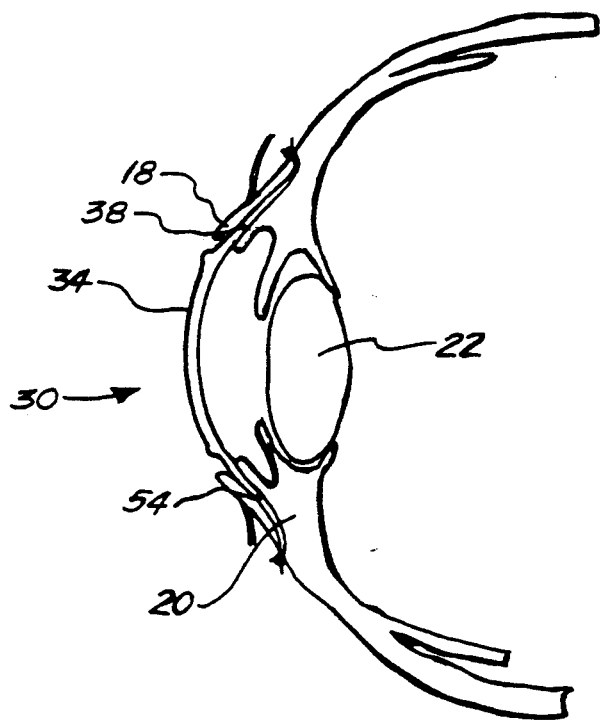

As may be appreciated, the length of the extensions 54 help in placing the extensions in the tunnels, by lengthening the extensions 54, the extensions are more easily manipulated and placed in the tunnels. All excess extension 54 material, approximately, for example seven-eight millimeters, is then cut off, and the free ends of the extensions 54 thus extend into the sclera a suitable distance, such as for example two millimeters (FIG. 5). The extensions 54 thus remain in the tunnels unexposed, with their free ends extending into the sclera.

Thus, the extensions 54 allow forward progression of fluid, by means of the pores of the extensions 54, from the anterior chamber, to allow adequate nutrition of the sclera and to avoid degeneration of any remaining corneal stroma. The annular porous portion 42 and extensions 54 allow fibrous ingrowth of the tissues surrounding portion 42 and extension 54 into the pores for anchoring the skirt 38 to the tissue of the sclera and any remaining corneal tissue.

Further connective tissue ingrowth into the extensions creates a very clear apposition of the corneal limbus to the implant, thus sealing the implant into place. Since the ingrowth surrounds the prosthesis, no aqueous fluid can leak past the implant, and no direct path for pathogens into the eye will exist.

As may be appreciated, the pore size controls the rate of cellular ingrowth during the postoperative recovery period, with the smaller pores generally needing a longer period of recovery for adequate cellular ingrowth. In general the range for pore sizes may range between preferably for example 25-90 microns and have a mean deviation of ± ten microns. A particularly suitable mean pore size is for example sixty microns, thus providing a suitable shortened postoperative recovery period, while providing adequate skirt body. Further, a suitable matrix minimal tensile strength would be for example 5000 PSI to insure integrity of the material.

SECOND, ACCOMMODATING, INTRAOCULAR LENS EMBODIMENT

FIGS. 4, 4A & 6

Figure 4A:
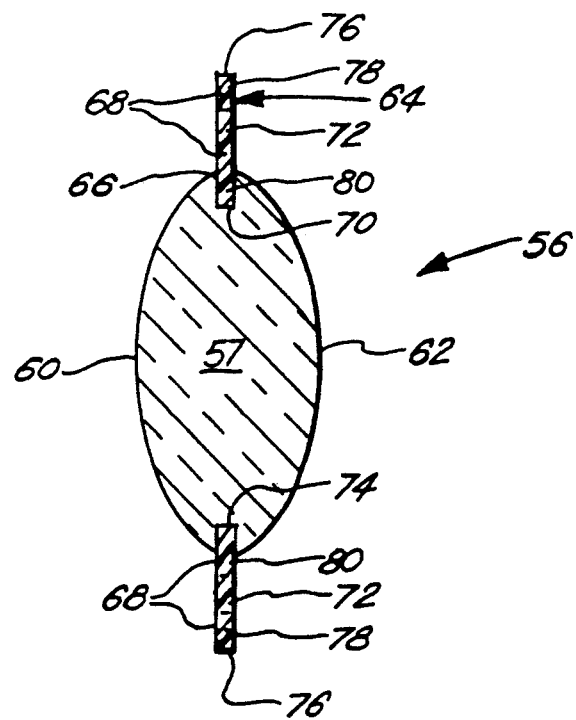

Referring to FIGS. 4 and 4A, a second embodiment of the prosthesis 56 suitable as a replacement lens for the posterior lens of the eye is shown.

The prosthesis 56 includes an optical element 57 having at least one convex anterior 60 and a posterior 62 surface. The optical element 57 is elastomeric and of a suitable material such as the aforementioned hydrophilic, optical polyurethane so that it may be varied to focus on objects that are close or far away.

Accordingly it will be necessary to decide on the mean power of the lens preoperatively. This can be accomplished, for example, as mentioned above by performing an ultrasound scan and/or evaluating the patient's refraction preoperatively and then making a clinical estimate of the proper power of the lens in order to determine proper refraction of the eye. Hence, the optical element 57 is a nonrigid lens, that permits the corrective power of the lens to be changed after implantation thereof into the eye.

An annular skirt 64 extends radially from the peripheral edge 66 of the optical element 57 and encircles the element 57. The annular skirt 64 may be a fluorocarbon having a low coefficient of friction such as polytetrafluoroethylene. A suitable form is for example Goretex obtained from W. L. Gore's & Associates, Inc., of Flagstaff, Ariz. The skirt 64 preferably has a diameter of for example thirteen millimeters and a thickness of for example 0.5 millimeters. The material should be examined microscopically for a clean, inclusion free pores, and the matrix tensile strength is measured for minimum strength.

An annular porous portion 68 is included with the skirt and surrounds element 68. As may be appreciated, the skirt material provides the porous portion and in general has a pore size of for example less than 90 microns, which have been found suitable for purposes which are discussed below.

The skirt 64 is rounded and has a central opening 70 in which the optical element 57 is disposed.

The optical element 57 is permanently mated to the skirt 64 during the formation of the optical element 57. In general, this may be accomplished by centering the annular skirt 64 between a pair of opposed hemispherical molds having facing convex surfaces and clamping the molds together with the annular skirt 64 sandwiched between the molds.

A polymerization mixture is then introduced into the space between the molds, which overlap radially into the porous material for forming the lens element. The overlapping polymerization mixture, which extends annularly around the inner portion of the skirt 64, is allowed to interpenetrate into the porous material for bonding the ocular element 57 to its skirt 64.

A preferred embodiment for the skirt 64 has an annular portion 72, which is compressed by any suitable means and extends around the skirt 64. The annular portion 72 is located radially outward from the inner periphery 74 of the skirt 64 and radially inward from the outer periphery 76 of the skirt 64. By compressing a portion of the skirt 64, a closed pore barrier 72 having a radial thickness of one millimeter may be formed which extends around the skirt 64 between its inner and outer peripheries 74, 76.

Hence, suitable dimensions for the skirt 64 after compression would be a two or three millimeter radial thickness annular open pore ingrowth space 78, which extends radially inward from the outer periphery 76 of the skirt 64; a one millimeter radial thickness annular close pore barrier 72; and a one millimeter radial thickness open pore annular bonding portion 80, which extends radially outward from the inner periphery 74 of the skirt 64 and which surrounds opening 70 for interpenetration and bonding of the optical element 57 to the skirt 64. Accordingly, the closed pore barrier 72 will prevent fluid communication between the ingrowth space 78 and the open pore annular bonding portion 80.

For exemplary purposes and as may be appreciated, the central opening 70 may be formed in a thirteen millimeter diameter skirt 64 by any suitable means, such as for example a nine millimeter trephine, and the pores at a one millimeter radius from the trephined opening 70, and a one millimeter wide ring outward may be compressed close to form the close pore barrier 72 by using for example a warm press.

After forming, the prosthesis 56 may be fully equilibrated in saline and sterilized in hydrogen peroxide before implantation.

For implanting, the patient is anesthetized, and for example a small three-four millimeter incision is made. The pupil is made to dilate with an appropriate percent opthane administered to the anterior eye chamber. The prosthesis 56 is inserted through the incision the opening in the iris and manipulated into the capsular bag.

The natural lens 22 of the eye can be removed by any manner known to those skilled in the art, such as for example, phacoemulsification, or extracapsular extraction. As may be appreciated, the entire lens 22 is to be removed from inside the capsular bag while leaving all of the suspensory ligaments or surrounding tissue, zonular fibers 29 of the ciliary body 28 intact.

As may be appreciated, the removal of the natural lens of the eye forms a void in the eye surrounded by the ciliary body, in which the prosthesis 56 may be located with its annular skirt 64 in contact with the lens capsule 122 which is connected by the zonular fibers 29 to the ciliary body 28 which surrounds the normal lens of the eye.

Once the prosthesis 56 has been manipulated into the position, the pupil may be made to contract by using for example an acetylcholine solution, the anterior chamber washed using for example 0.9% sterile saline solution and reformed using healon, and the incision may be sutured closed using a suitable filament such as for example a 9-0 nylon. An antibiotic solution is administered under the conjunctiva for purpose of prophylaxis, for example gentamicin being used for that purpose.

Figure 6:
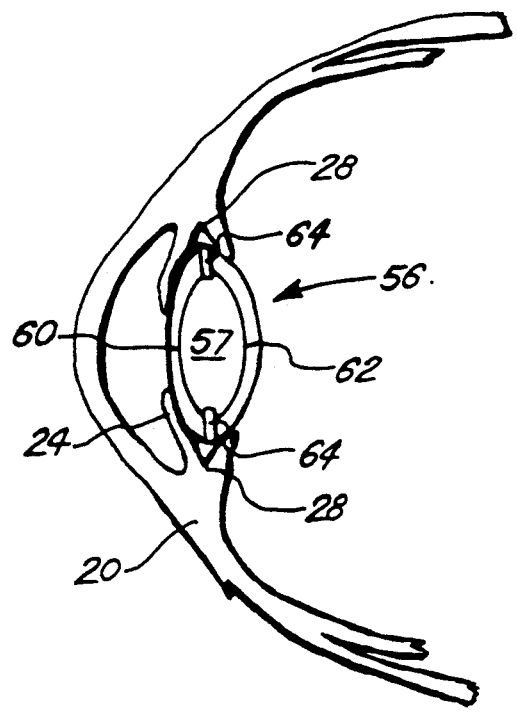
FIG. 6 is a side, cutaway view of the eye with the second embodiment (FIGS. 4 and 4A) implanted.

Thereafter the prosthesis 56 stabilizes and rapidly connects to the lens capsule 122, as shown in FIG. 6, through fibrous ingrowth into the pores of the ingrowth space 78. Attached to the lens capsule 122 are the zonular fibers 29 which connect to the ciliary body 28 and transmit the contraction and relaxation forces of the ciliary muscle 202 to the lens capsule 122. Since all material is flexible, the prosthesis 56 and its ocular element 57 will change shape in response to ciliary body contraction just as the normal lens does, allowing the optical element 57 to focus an image through the vitreous chamber and onto the retina in the back of the eye, in a manner similar to the normal lens of the eye.

The ingrowth space 78 allows fibrous ingrowth of the surrounding tissues into the pores for anchoring the skirt 64.

In a similar manner, the pore size controls the rate of cellular ingrowth during the postoperative recovery period, with the smaller pores generally needing a longer period of recovery for adequate cellular ingrowth. In general the range for pore sizes may likewise be between 15-90 microns and have a mean deviation of ± ten microns. Likewise a particularly suitable mean pore size is sixty microns, thus providing a suitable shortened postoperative recovery period, while providing adequate skirt body. Likewise a suitable matrix minimal tensile strength would be for example 5000 PSI to insure good integrity of the material.

A further, exemplary, currently preferred, method of implantation is summarized below.

The patient is anesthetized, and the eye is draped and prepped. A Basic Salt Solution I.V. is started with 0.30 units/cc Heprin.

Then a 3-4 mm incision is made superiorly with a superblade, followed by a small incision in the anterior capsule using for example a cystome. The lens nucleus is phacoemulcified with the cortex removed by irrigation and aspiration.

The new intraocular prosthetic lens is rolled and inserted into the capsular bag, with forceps holding onto one end or a soft intraocular lens (IOL) inserting device (sometimes referred to as a "shooter".) Upon release of the forceps or soft IOL inserting device, the intraocular prosthesis begins to unroll in the bag.

A blunt ended positioner is used to gently check that the prosthesis was completely unfolded in the bag and centrally positioned. Healon is used to maintain the anterior chamber during the operation.

The wound is closed with for example 10-0 nylon sutures. A subconjunctival injection of "Decadron" and "Garamycin" is given, before the patient is returned to recovery.

The lens forms one of the refractive media of the eyes. It is perfectly transparent and situated between the iris and vitreous body of the eye. Its function is to finefocus light from objects at variable distances onto the retina. The refractive power of the lens is dependent on its shape, power of curvature and refractive index.

The interior of the lens is composed of two areas (the nucleus and the cortex) of different optical densities although there is no sharp boundary between these portions. The lens is completely surrounded and enclosed by a membrane called the lens capsule. The capsule is elastic and possesses a fine fibrillar structure. It is composed of a basement membrane lined interiorly with a layer of epithelial cells on the anterior and equator regions. The zonular lamella forms the outside layer of the capsule and it is to this layer that the zonule fibers attach and suspend the lens from the ciliary body. The lens is supported by the ciliary body much in the same way a hammock is hung between two posts. The zonule fibers serve as the ropes and are considered part of the ciliary muscle apparatus. The zonule fibers themselves are elastic in nature and are capable of stretching and relaxing in response to ciliary muscle and choroid movement.

The result of the zonule fiber action, when they stretch and relax, is to change the curvature of the lens. When the ciliary muscle is relaxed, the zonules are under tension. The tension of the zonule fibers pulls the lens capsule and lens toward their equator so that the thickness of the lens is decreased or flattened. When the ciliary muscle contracts, the tension on the zonules relaxes. In turn, the tension on the lens capsule and lens relaxes. When the zonule fibers relax their tension, the elastic nature of the lens capsule allows the lens to thicken in anterior to posterior diameter. It is through the action of the ciliary muscle apparatus, (composed of the ciliary muscle), chorid and zonular fibers, changing the lens shape that the dioptic power of the lens is changed. The process by means of which the dioptic power of the lens, and therefore the eye, is changed is called accommodation.

Accommodation of the lens focuses incoming light onto the retina. When the choroid and ciliary muscle are relaxed, the parallel light rays from the a very distant object are focused on the retina. The image of the object is clear and shows visual acuity is at a maximum. If the object is brought closer to the eye and the eye remains unchanged, the light will be focused behind the retina. The rays of light, in being intercepted by the retina, would form a blur instead of the image of a sharp object. Since the distance between the lens and retina is fixed in the human eye, the refractive power of the lens must increase to focus the light onto the retina.

When the prosthesis is placed in the lens capsule, after removal of the lens interior, the prosthesis fills the equatorial diameter of the capsular bag so that the ingrowth material touches the bag along the entire equatorial circumference. The ingrowth material allows fibrous ingrowth of the surrounding tissues into the pores securely anchoring the prosthesis in the capsular bag. The ingrowth may be attributed to the pressure of the skirt against the equator of the capsule slightly injuring, aggravating or inflaming the germinative epithelial cells and the lens capsule itself in that area. The elastic properties of the capsule might also enhance the degree to which tissue ingrowth occurs. Once cut for entry into the lens, the anterior capsule, lined with epithelial cells, retracts slightly and lays more closely adjacent to the skirt of the intraocular lens (IOL). The lens capsule is generally considered to be a non-cellular laminated membrane composed mainly of an insoluble protein with about 10% carbohydrate which is similar but not identical to collagen. Yet, the lens capsule is not an inert membrane. Even after removal of its epithelium the capsule shows glycolytic activity. It has been documented that when inert implants are placed in contact with tissue a specialized form of wound repair, encapsulation and organization, occurs. The specialized form of wound repair consists of the development of granulation tissue and secretion of collagen. It can be initiated by granulomatous inflammation; however, it is not dependent only on that type of initiation. Granulation tissue is where the elaboration of reparative collagen takes place, although collagen is also slowly formed in uninjured tissue. The exact reason and mechanism as to why and how cells, whose normal function does not include fibrin formation, start the wound repair responce, i.e., fibrin/collagen formation, has yet to be elucidated only the fact that they do is known. The degree of granulation tissue development around prosthetic implants relates to their size and surface characteristics, as well as their degree of chemical inertness. Large, rough-surfaced implants invoke extensive granulation tissue development.

Once secured in the bag, since all the materials are flexible, the prosthesis and its ocular element will change shape in response to the ciliary muscle apparatus just as the normal lens does, allowing the optical element to focus an image through the vitreous chamber and onto the retina in the back of the eye, in a manner similar to the normal lens of the eye.

The embodiments and related methodologies described herein in detail for exemplary purposes are of course subject to many different variations in structure, design, methodology and application. Because many varying and different embodiments may be made within the scope of the inventive concept(s) herein taught, and because many modifications may be made in the embodiments herein detailed in accordance with the descriptive requirements of the law, it is to be understood that the details herein are to be interpreted as illustrative and not in a limiting sense.

What is claimed is:

1. An ocular prosthesis for use as an implant within the eye socket region of a patient, within the patient's eye or on the outer surface of the patient's eye, comprising:
   a) a prosthesis body that is positioned during use in the eye socket region of a patient's body, said region being exposed to the external environment and to the threat of pathogen travel from outside the patient's body;
   b) the prosthesis body including tissue attachment means that includes a non-resorbable, non-dissolving porous polymer material with a port size greater than 20 microns, and wherein the pores of the porous polymer material form a tissue attachment site on a first outer surface of the prosthesis that allows tissue ingrowth by surrounding ocular tissue; and c) the prosthesis body including a solid or closed-pore polymer layer coextensive with the tissue attachment site that forms a barrier against generally transverse fluid or pathogen travel from a second outer surface which opposes said first outer surface, to the tissue attachment site.

2. An ocular prosthesis for use as an implant within the eye socket region of a patient, within the patient's eye or on the outer surface of the patient's eye comprising:

a) a prosthesis body having tissue adhesion means on a first outer surface of the prosthesis body for forming a bond between the eye tissue and the prosthesis;

b) wherein the tissue adhesion means comprises a portion formed of a porous polymer material having pores that enable connection to surrounding ocular tissue, wherein the pores of the polymer define a tissue attachment site;

c) the prosthesis body having means for impeding fluid leakage past the implant at the tissue attachment site; and d) wherein said means for impeding comprises a portion formed of a solid or closed-pore polymer material coextensive with the tissue attachment site so that a barrier is formed against generally transverse fluid and pathogen penetration rom a second outer surface which opposes said first outer surface to the tissue attachment site.

3. An ocular prosthesis comprising:

a) a prosthesis body that includes a first outer surface of a porous polymer material having a pore size of about twenty to ninety (20–90) microns for forming a tissue adhesion surface defining a tissue attachment site for attachment of surrounding ocular tissue;

b) the body having a means for impeding fluid and pathogens from leaking past the implant at the tissue attachment site; and c) wherein said means for impeding comprises a portion formed of a solid or closed-pore polymer material coextensive with the tissue attachment site so that a barrier is formed against generally transverse fluid and pathogen penetration from a second outer surface which opposes said first outer surface to the tissue attachment site.

4. The prosthesis of claims 1, 2, or 3 wherein the polymer is of a material that will not unravel when cut.

5. The prosthesis of claim 1 wherein the polymer forms a porous layer and there is an adjacent non-porous layer so that a barrier is defined against bacterial penetration or fluid leakage.

6. The prosthesis of claims 1, 2, or 3 wherein the non-porous layer is a non-porous polyurethane, polyacrylate polymethacrylate, polysiloxane, biopolymer, or a copolymer of these polymers.

7. The prosthesis of claims 1, 2, or 3 wherein: the porous polymer material comprises a material from the group consisting of polyurethane, polypropylene-polybutylene copolymer, polytetrafluoroethylene, polyothoesters, polyesters, polyethylene terephthalate, polyacrylate, and a silicone based polymer.

8. The prosthesis of claims 1, 2, or 3, wherein the porous polymer material is an expanded polymer foam, fabric or mesh.

9. The prosthesis of claims 1, 2, or 3, wherein the solid polymer layer is substantially impermeable to fluids.

* * * * *